US006585300B1

(12) United States Patent
Rajala et al.

(10) Patent No.: US 6,585,300 B1
(45) Date of Patent: Jul. 1, 2003

(54) APPARATUS FOR APPLYING STRING TO TAMPON PLEDGETS

(75) Inventors: Gregory J. Rajala, Neenah, WI (US); Brandon S. May, Neenah, WI (US); Troy L. Tipton, Neenah, WI (US); Karl V. Fredrick, Neenah, WI (US); Thomas Bohlmann, Chesterfield, VA (US); Edwin L. Cutright, Mt. Pleasant, SC (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/036,089

(22) Filed: Dec. 28, 2001

(51) Int. Cl.$^7$ .............................................. A01D 59/04
(52) U.S. Cl. ........................................ 289/2; 289/18.1
(58) Field of Search .............................. 289/1.2, 1.5, 2, 289/16, 17, 18.1; 19/144; 28/118, 119, 120; 112/470.21, 475.17, 10, 6, 11, 116, 121, 470.22; 604/385.17, 385.18, 904

(56) References Cited

U.S. PATENT DOCUMENTS

| | | | | |
|---|---|---|---|---|
| 3,348,866 A | * | 10/1967 | Etz | 289/18.1 |
| 3,814,469 A | * | 6/1974 | Simon | 289/1.5 |
| 3,940,169 A | * | 2/1976 | Kock | 289/1.5 |
| 3,970,022 A | * | 7/1976 | Kopatz et al. | 112/475.08 |
| 4,006,515 A | | 2/1977 | Mast, Jr. | |
| 4,144,623 A | | 3/1979 | Steffens | |
| 4,490,894 A | | 1/1985 | Friese | |
| 4,836,587 A | | 6/1989 | Hinzmann | |
| 5,566,435 A | | 10/1996 | Brown, Jr. | |
| 6,213,040 B1 | | 4/2001 | Shepard | |

FOREIGN PATENT DOCUMENTS

| | | | | |
|---|---|---|---|---|
| DE | 2701604 | * | 7/1978 | A61F/13/20 |
| WO | WO 95/27458 | * | 10/1995 | A61F/13/20 |

* cited by examiner

Primary Examiner—Gary L Welch
(74) Attorney, Agent, or Firm—Senniger, Powers, Leavitt & Roedel (57) ABSTRACT

Method of and apparatus for applying withdrawal strings to tampon pledgets wherein string is pneumatically looped around a pledget, the ends of the loop are knotted, and the knotted loop is driven through a hole in the pledget.

9 Claims, 12 Drawing Sheets

APPARATUS FOR APPLYING STRING TO TAMPON PLEDGETS

BACKGROUND OF THE INVENTION

This invention relates to a method of and apparatus for applying a string to a tampon pledget and more particularly to a method of and apparatus for automatically knotting and attaching strings to tampon pledgets in relatively high speed production.

Strings may be attached to tampon pledgets using various methods. Some of these methods may be accomplished manually and others require various apparatus. Many of these apparatus are highly complex, requiring significant initial capital expenditures. Examples of such apparatus include those disclosed in U.S. Pat. No. 4,144,623 issued Mar. 20, 1979, entitled, "Process for the Production of Tampon Blanks"; U.S. Pat. No. 4,490,894 issued Jan. 1, 1985, entitled, "Apparatus for Attaching a Withdrawal Cord to a Tampon"; U.S. Pat. No. 5,566,435 issued Oct. 22, 1996, entitled, "Method of Attaching a Tampon Withdrawal Cord with an Overhand Hitch Knot"; and U.S. Pat. No. 6,213,040B1 issued Apr. 10, 2001, entitled, "Apparatus for High-Speed Lacing of an Article". The complexity of these apparatus can make maintenance and repair of the apparatus difficult and costly. Thus, there is a need for a relatively simple high speed apparatus and method for attaching strings to tampon pledgets.

SUMMARY OF THE INVENTION

In general, a method of the present invention is for applying a withdrawal string to a tampon pledget having opposite faces and includes positioning the string to extend across one of said faces of the pledget, said string thereby having a generally central portion on said one face and reaches extending on both sides of the pledget, acting on said reaches pneumatically to form the string into a loop looped around the pledget, securing together the end portions of the reaches in the loop, and moving the secured-together end portions through the pledget thereby bringing part of the loop including the secured-together end portions thereof to extend out from said one face of the pledget.

In general, apparatus of the invention includes a string feeder for positioning a string to extend across one of the faces of the pledget, said string thereby having a generally central portion on said one face and reaches extending on both sides of the pledget, a pneumatic system operable on said reaches pneumatically to form the string into a loop looped around the pledget, a knotter for knotting together end portions of the reaches in the loop, and a probe movable to drive the knotted end portion of the loop through the pledget thereby bringing part of the loop including the secured-together end portions thereof to extend out from said one face of the pledget.

Other features will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

FIGS. 1–6 schematically illustrate a method of the present invention which is applicable to a tampon pledget generally designated by the reference numeral 1. The pledget 1 is of rectangular parallelepiped (i.e., brick-shaped) form having opposite rectangular faces 3, 5; sides 7, 9 and ends 11, 13. As viewed in FIGS. 1–6, face 3 is the front face, face 5 is the rear or back face. The pledget, which is illustrated in a vertical orientation, has a hole 15 extending between the faces 3, 5 centered between its sides 7, 9 and located between a center of its length and its lower end 13. The pledget 1 becomes a tampon when a withdrawal string, generally designated by 17, is applied to it in accordance with this invention.

Figure 1:
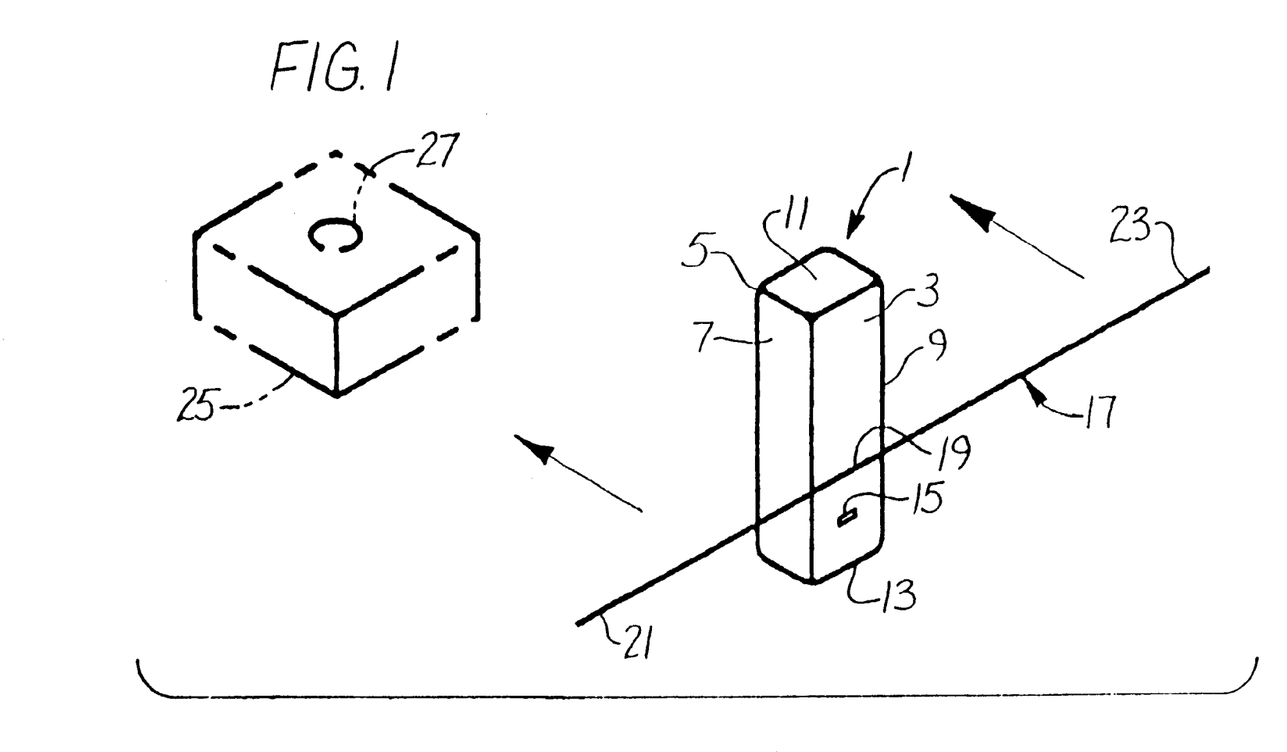
FIGS. 1–6 are schematics illustrating steps of a method of the present invention.
Figure 2:
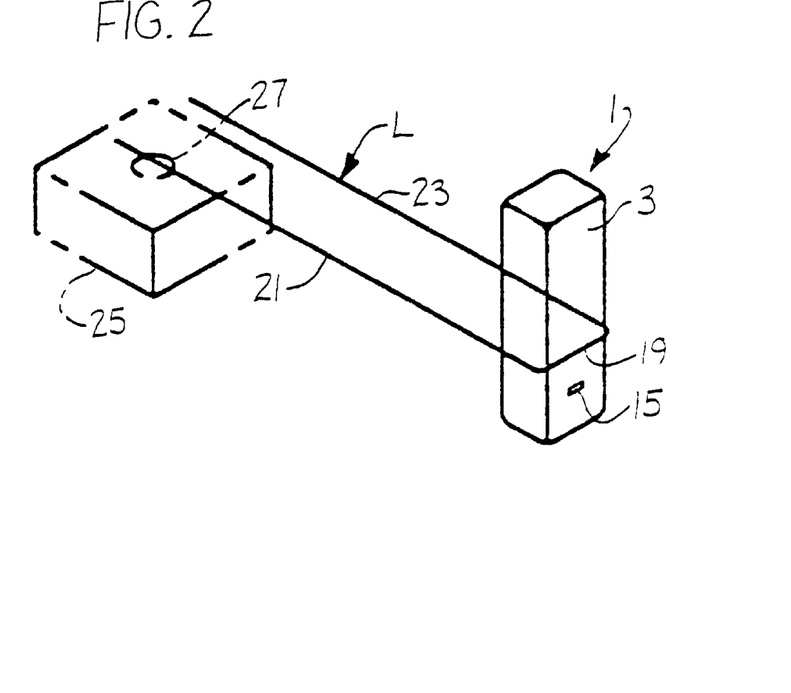

As illustrated in FIG. 1, the first step in the method of this invention is to position a length of string 17, which becomes the withdrawal string for a tampon, so it, extends laterally across one of the faces, specifically face 3 as shown, of the pledget. So positioned, the string 17, which may be, for example, about 15.5 inches long, has a generally central portion 19 on the front face 3, and reaches 21, 23 extending outward from both sides 7, 9 of the pledget. A conventional pneumatic knotter 25 having a hole 27 for receiving the end portions of the reaches 21, 23 is positioned behind the pledget 1.

In accordance with this invention, the reaches 21, 23 are acted on pneumatically to form the string 17 into a loop, generally designated by L (FIG. 2), looped around the pledget 1. In one embodiment, the reaches 21, 23 are acted on pneumatically by suction to draw them back and thereby form the string 17 into the loop L. The suction is produced by drawing a vacuum behind the pledget 1, as indicated by the arrows in FIG. 1. The central portion 19 of the string then becomes the bight of the loop L and the reaches 21, 23 become the side reaches of the loop.

The end portions of the reaches 21, 23 in the loop L (i.e., the rearward ends of the reaches) are secured together by the knotter 25 to form a knot 29 (see FIGS. 5–8). The knot 29 in the ends of the reaches 21, 23 is made by pneumatically pulling them into the knotter, as shown in FIG. 3 for action on the ends by the mechanism of the knotter to tie the ends together.

Figure 3:
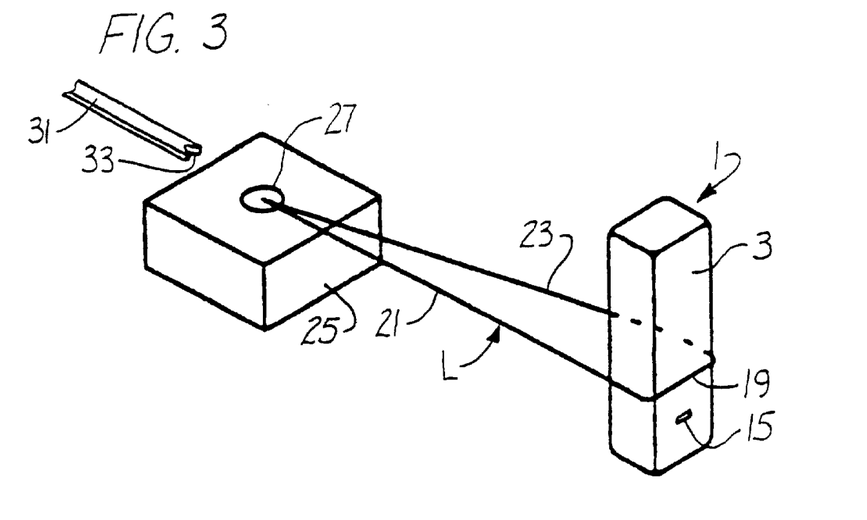
Figure 4:
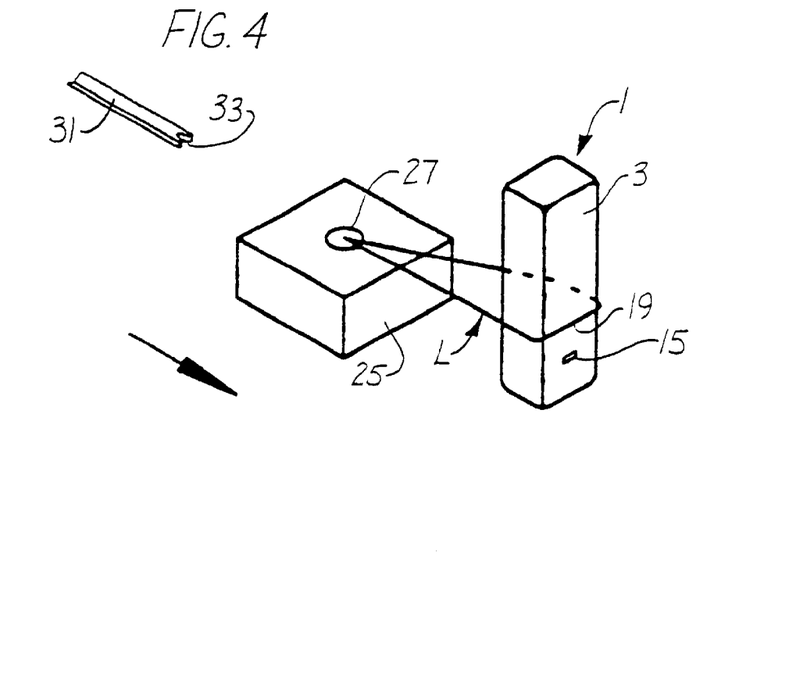
Figure 5:
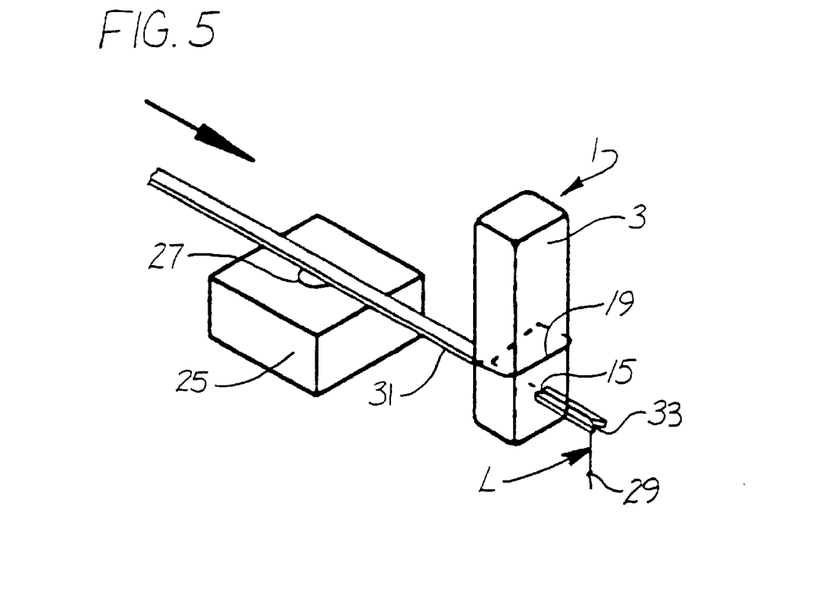
Figure 6:
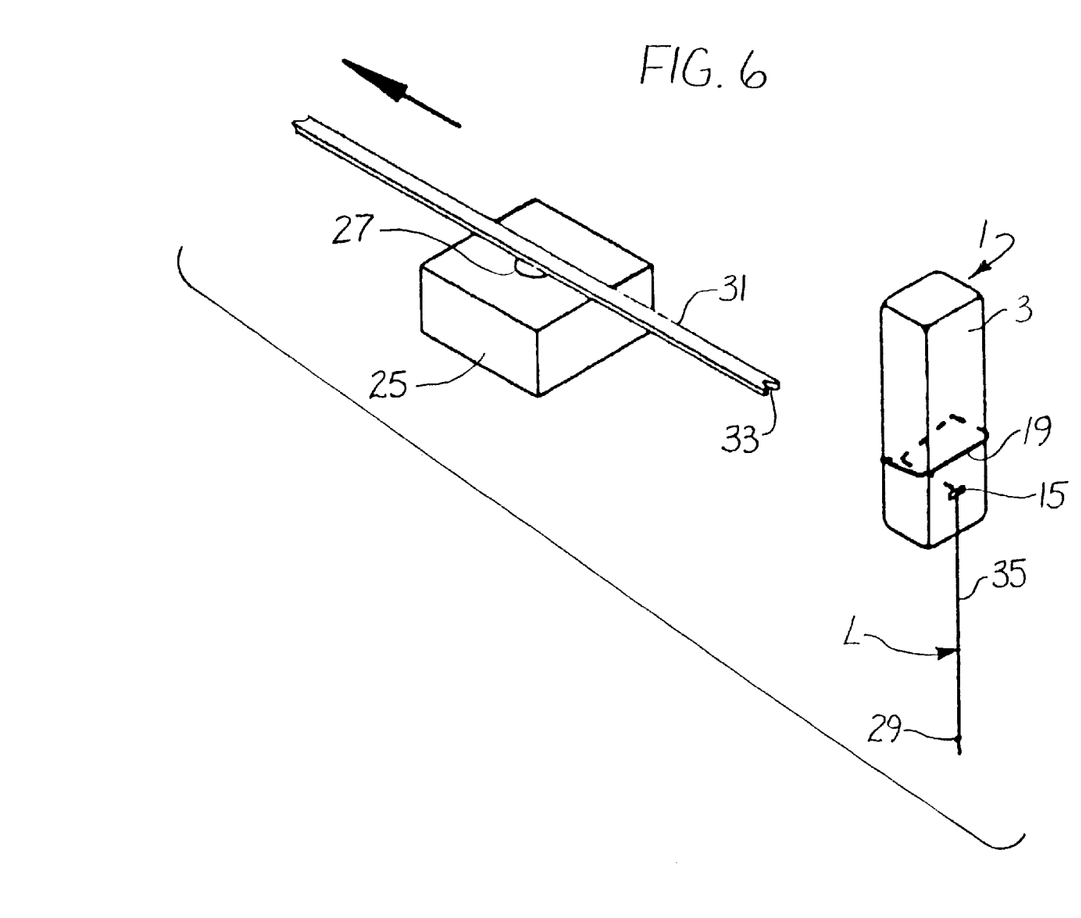
Figure 7:
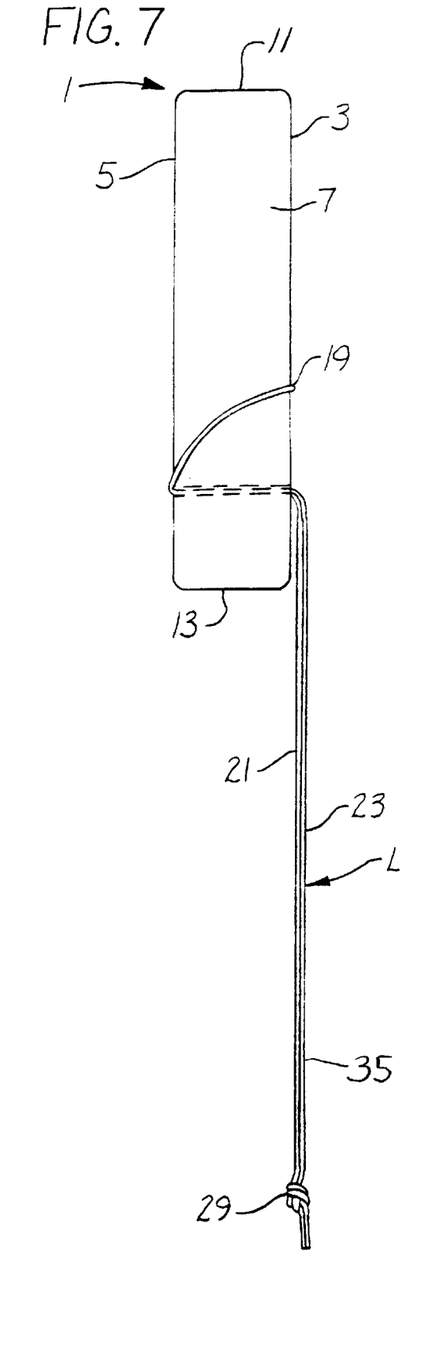
FIG. 7 is a side elevation of a tampon having its withdrawal string as applied according to FIGS. 1–6.
Figure 8:
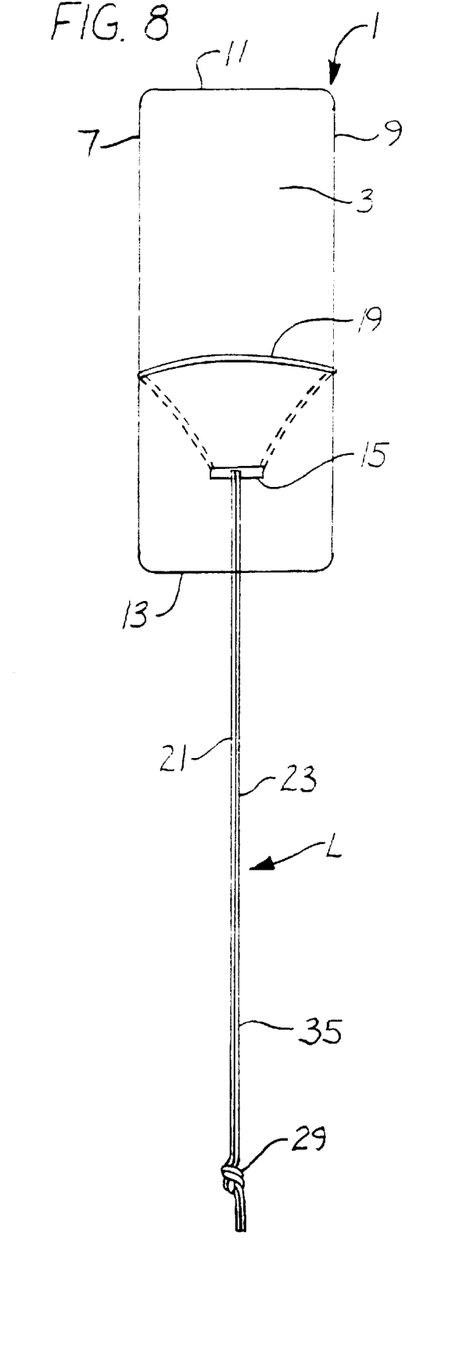
FIG. 8 is a front elevation of the tampon of FIG. 7.

After the ends of the reaches 21, 23 of the loop L are knotted, the knotter 25 moves forward from its FIG. 3 position toward the pledget 1 as depicted in FIG. 4. The knotted end of the loop L remains in the knotter 25 under the influence of the vacuum drawn by the knotter as the knotter moves forward. Then, a probe or needle 31 moves lengthwise above the knotter 25 in line with the hole 15 in the pledget 1 from a rearward or retracted position as illustrated in FIGS. 3 and 4 to a forward or extended position as illustrated in FIG. 5. The tip 33 of the needle 31 has a notch (e.g, a v-shaped notch or u-shaped notch) for capturing the tied-together reaches 21, 23, pulling the looped string out of the knotter 25, and threading it through the hole 15. Finally, the needle 31 and knotter 25 are retracted as indicated by the arrow in FIG. 6, leaving the pledget 1 with the string 17 encircling the pledget and extending from the back face 5 to form a double-strand pendant 35 extending from hole 15 as shown in FIGS. 6–8.

Figure 9:
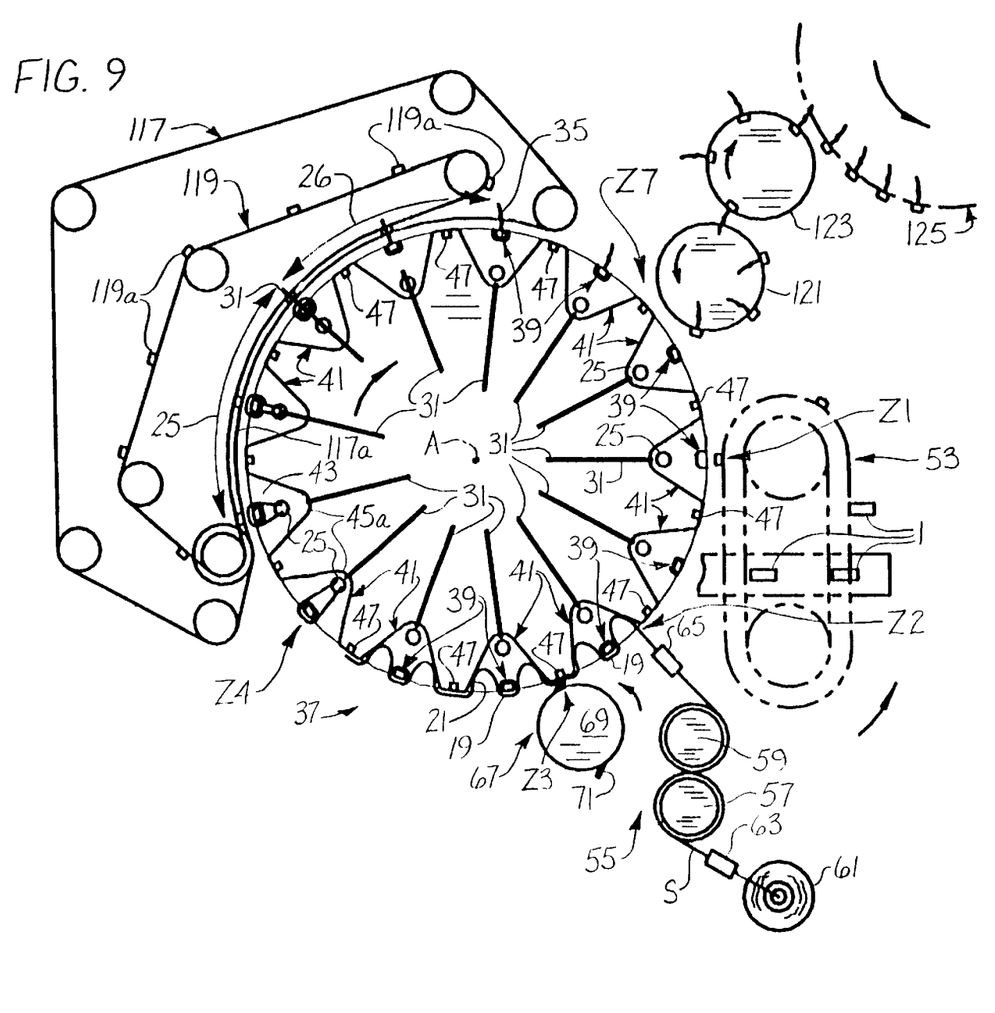
FIG. 9 is a schematic illustrating apparatus for carrying out the method of the invention.

FIG. 9 schematically illustrates the apparatus of the present invention for carrying out the above-described method of the invention and reference is made to FIGS. 10–15 for details. As schematically shown in FIG. 9 and detailed in FIGS. 10–14, the apparatus comprises a pledget conveyor, generally designated by 37, having a series of pledget holders 39 spaced at intervals thereabound (e.g., thirteen equally-spaced holders). Each holder 39 is formed for holding a pledget 1 with its front face 3 totally exposed and facing outward from the conveyor 37 and the lower part of its back (or rear) face 5 being exposed below the holder. Each holder 39 has a perforated back wall 39*a* and forwardly extending side walls 39*b* (see FIGS. 13 and 14), being of such height as to allow for the exposure of the lower part of the back face 5 of the pledget from just above the hole 15 down to its lower end 13. In one embodiment, the conveyor 37 comprises a circular turret rotatable in a horizontal plane on a central vertical axis A, and will be henceforth referred to as such. Spaced at equal intervals around the turret 37 adjacent its periphery is a series of outwardly opening chambers, each generally designated by 41. Each chamber 41 has a forward or outer part 43 (see FIG. 14) flaring outward from a rearward or inner part 45 which has an inner end 45*a*. Each chamber 41 is bisected by a radius of the turret. Each pledget holder 39 is generally centered on an open end of a respective outer chamber part 43. A series of anvils 47 (FIG. 9) is spaced at equal intervals around the turret 37 midway between the pledget holders 39 for engagement by a string cutter as will be subsequently described.

Figure 14:
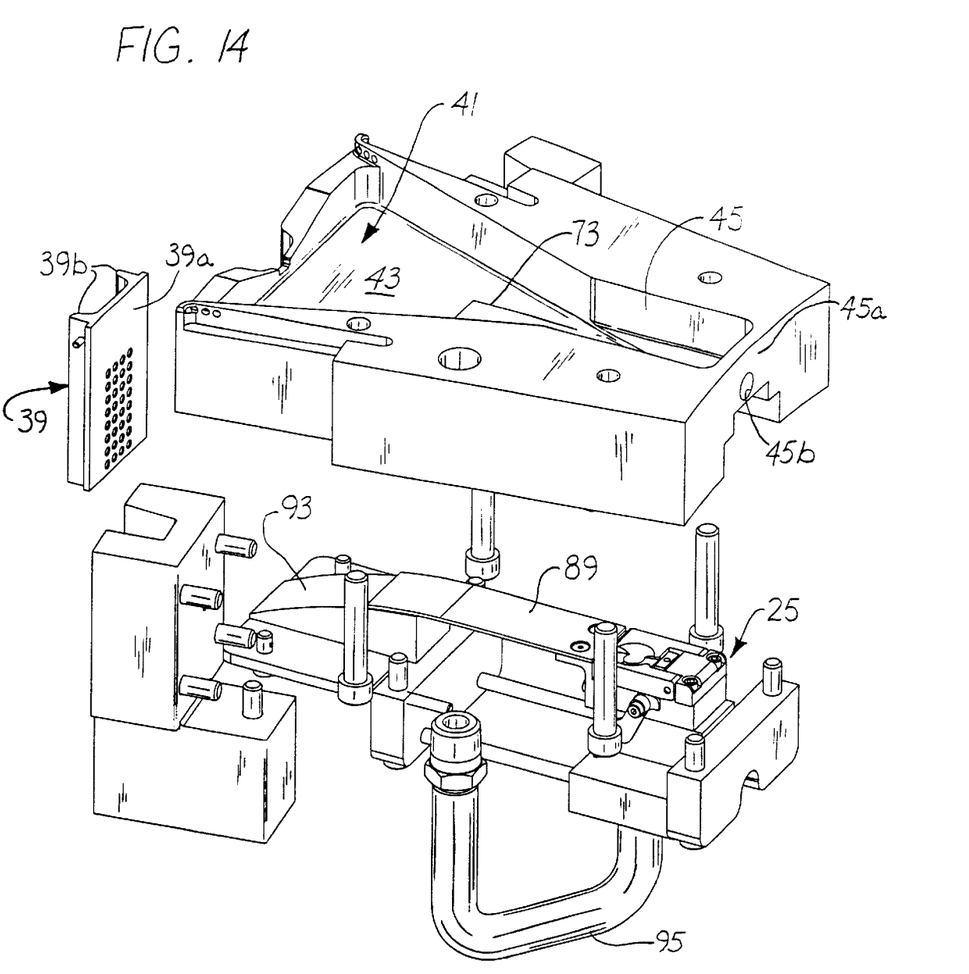
FIG. 14 is a partially separated view of the part shown in FIG. 13.
Figure 15:
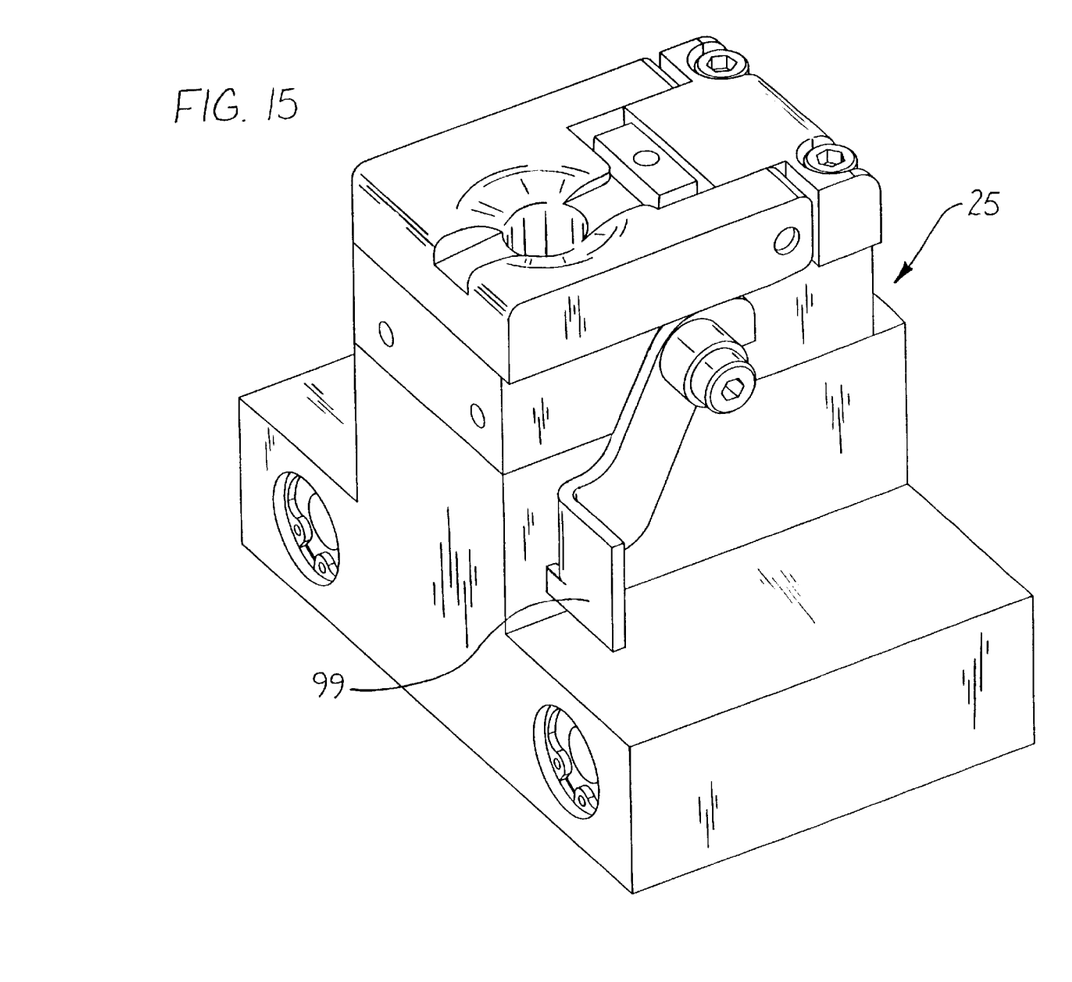
FIG. 15 is a perspective of a knotter component of the apparatus.

As noted and more particularly shown in FIG. 14, each pledget holder 39 comprises a generally U-shaped body arranged with its open side facing outwardly for receiving a pledget 1 with the front face 3 of the pledget totally exposed. The walls 39*a*, 39*b* of the holder 39 are short enough and so located as to hold a pledget 1 without covering the hole 15 near the lower end 13 of the pledget. A pledget delivery unit, generally designated by 53 (FIG. 9), delivers pledgets 1 to the turret 37 and transfers them to the pledget holders 39 as the holders move with the turret through a first zone Z1 along the endless (circular) path of the holders.

A string feeder, generally designated by 55 (FIG. 9), feeds string S to each pledget 1 at a second zone Z2 along the endless (circular) path of the holders 39. In one embodiment, the string feeder 55 is the same string feeder as disclosed and claimed in a co-assigned U.S. Patent Application of Gregory J. Rajala, filed Oct. 26, 2001, entitled "Feeding String" which is hereby incorporated by reference. Broadly, it comprises a pair of godet rolls 57, 59 which feed string S from a supply, specifically a cop 61, with a venturi 63 for retarding the string upstream from the godet rolls and a venturi 65 for accelerating the string downstream from the godet rolls as the string approaches the turret 37. The feeder 55 feeds the string S as illustrated to extend across the front face 3 of the pledget 1 traveling on its circular path through zone Z2.

A string cutter, generally designated by 67 (FIG. 9), is operable in a third zone Z3 along the endless (circular) path to cut the string S to length. The resultant withdrawal string 17 includes a central portion 19 extending across the front face 3 of the pledget 1 and reaches 21, 23 extending out from both sides of the pledget. The cutter 67 is a conventional rotary cutter cooperable with the anvils 47, comprising a rotor 69 having cutting blades 71 spaced therearound. A vacuum is drawn in each chamber 41 through vacuum line 72 (FIG. 10) when the chamber has passed through zone Z3, thereby holding the cut-off length of string 17 on the periphery of the turret 37 and initiating the drawing back of the reaches 21, 23 of the cut-off length of string to form the loop L. This may be referred to as the "looping vacuum".

Each knotter 25 is radially movable in its chamber 41 between a radially retracted position adjacent the inner end 45*a* of the chamber and a radially advanced position. The aforesaid looping vacuum is maintained until the loop L is completely formed and the ends are drawn down into the knotter (in its retracted position) as the chamber 41 rotates further and reaches a fourth zone Z4. The vacuum is maintained in the knotter 25 from the time when the loop L is drawn into the chamber 41 until the chamber is well past zone Z4 (as will be subsequently described). The knotter vacuum draws the ends of the loop L into the knotter 25 through its entry hole 27 and the knotter ties the knot 29. The knotter 25 is a commercially available item, namely a FALU knotter (which is air-operated) sold by K. Fassbind-Ludwig & Co. AG of Wagen by Jona, Switzerland.

Figure 10:
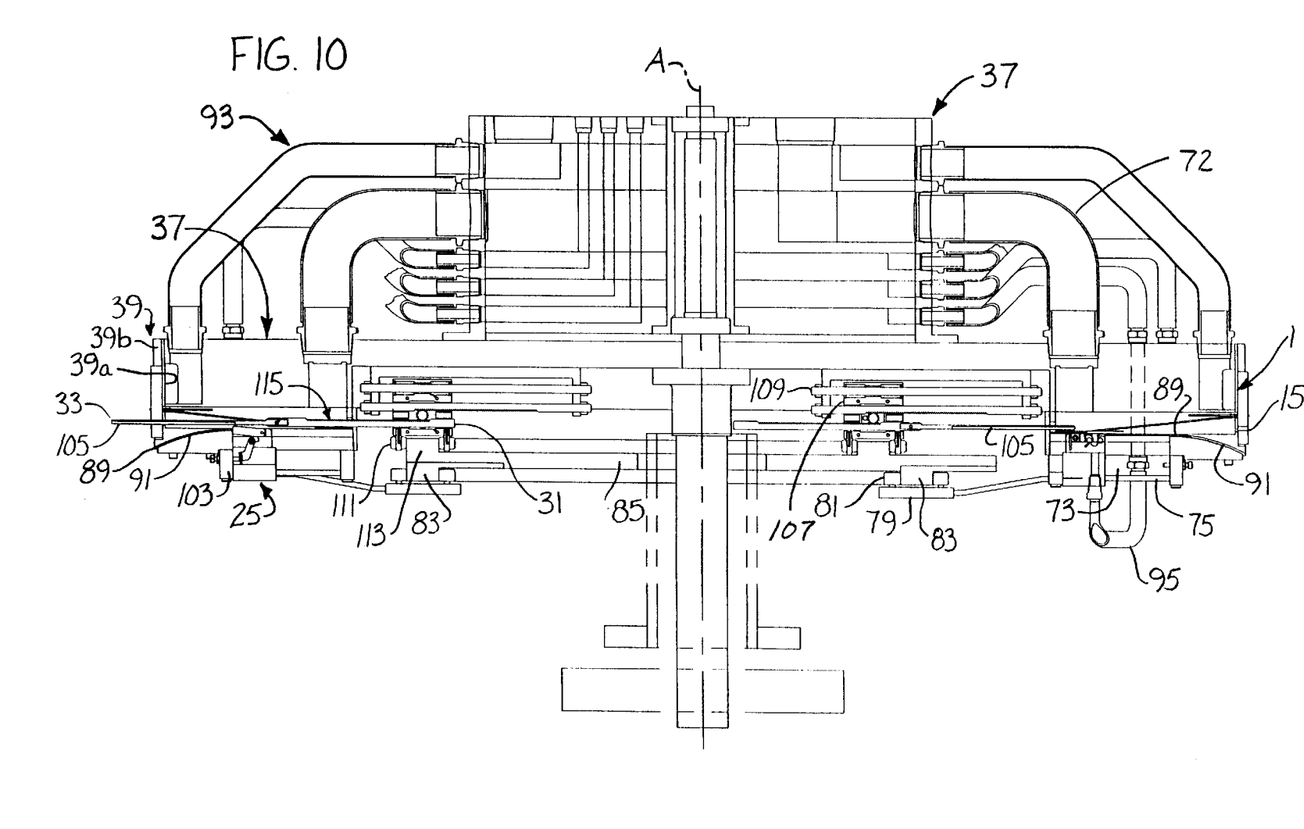
FIG. 10 is a section of the apparatus.
Figure 11:
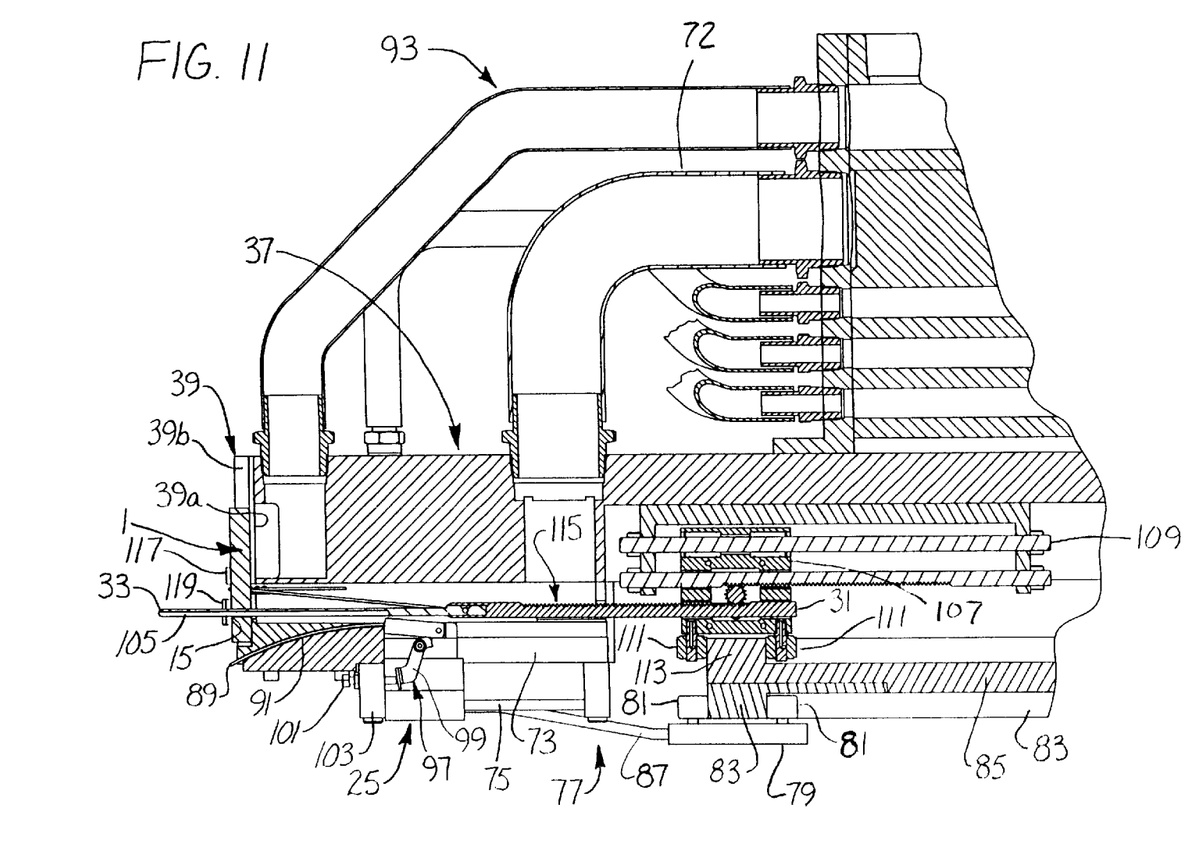
FIGS. 11 and 12 are enlarged fragmentary views of section shown in FIG. 10.
Figure 12:
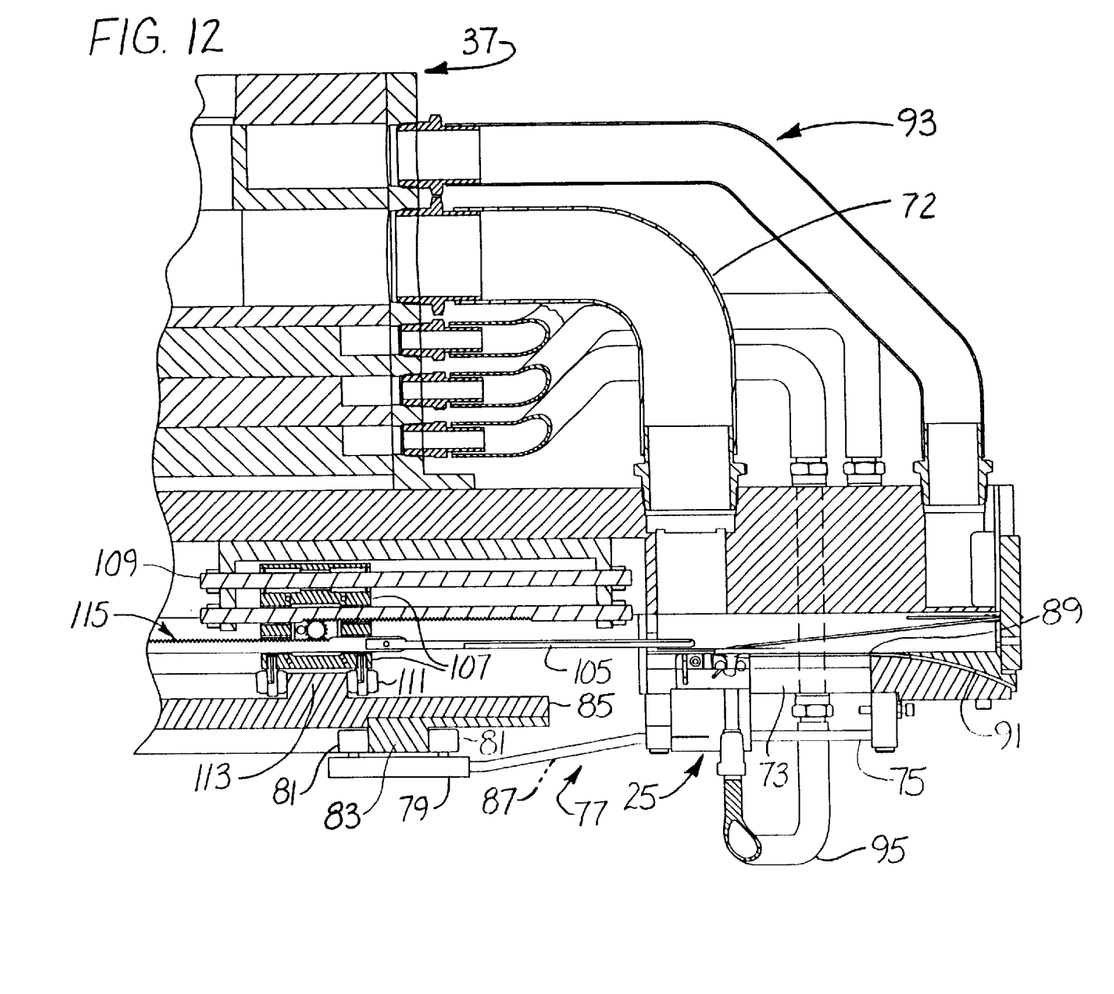
Figure 13:
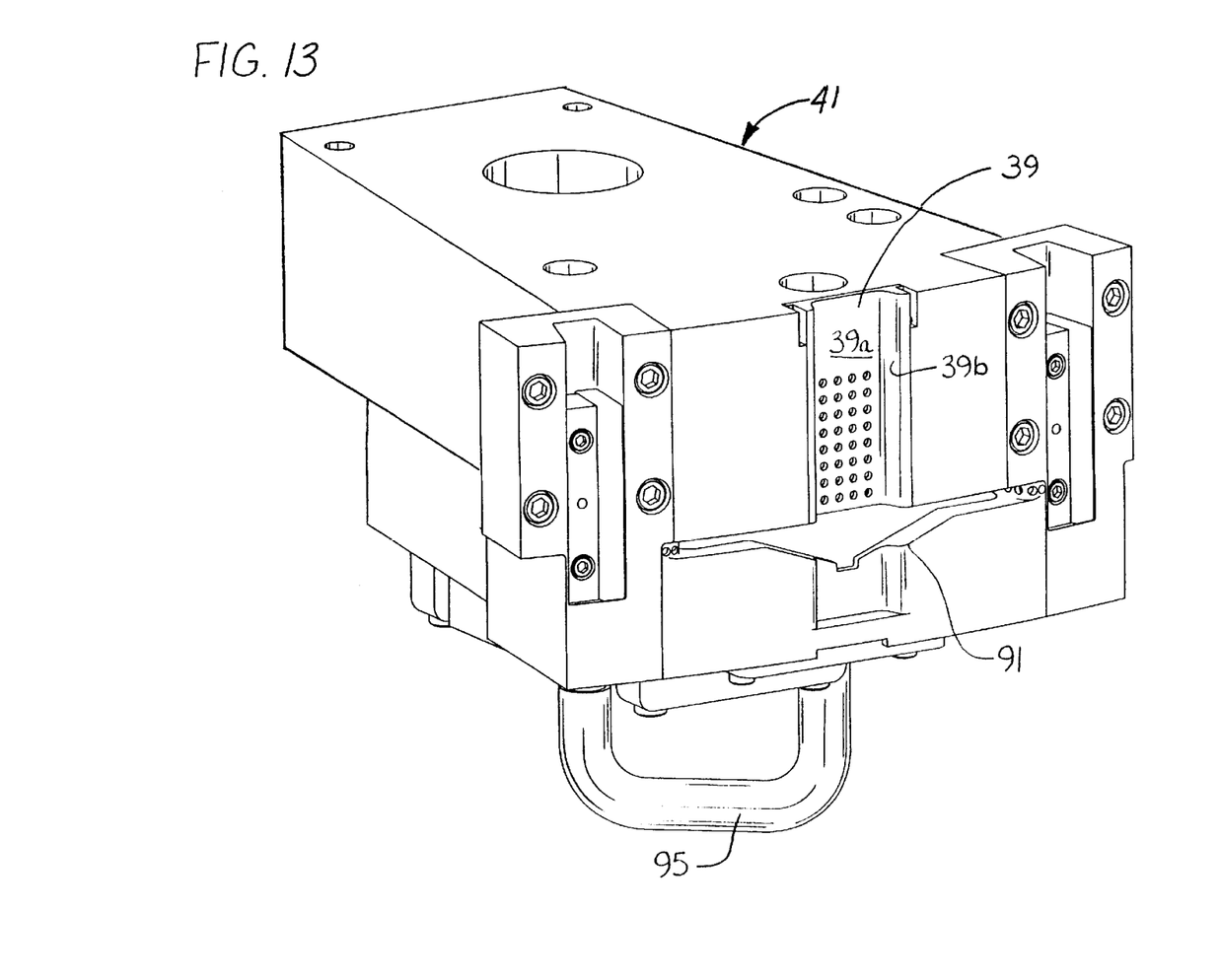
FIG. 13 is a perspective of part of the apparatus.

Each knotter 25 moves radially with respect to the turret 37 in a radial slot 73 (see FIGS. 10 and 14) formed in the bottom of the respective vacuum chamber 41 between the retracted inner position at the inner end of the slot (in which the knotter 25 is shown at the right of FIG. 10) and the extended outer position at the outer end of the slot (in which the knotter is shown at the left in FIG. 10). Each knotter 25 slides on radially extending guide rods 75 beneath the respective vacuum chamber 41 as it moves between its inner and outer positions. The knotters 25 are driven in and out by means generally indicated at 77 comprising a cam follower 79 having rollers 81 engaging an annular cam 83 fixed to a stationary annular plate 85 surrounding axis A under the turret 37 and a link 87 interconnecting the cam follower 79 and the knotter. The cam 83 maintains each knotter 25 in its inner position as the knotter travels from zone Z1 to zone Z4, then moves the knotter radially outward to its outer position as it exits zone Z4, and then returns the knotter to its inner position as it travels through zone Z5 and enters zone Z6.

A flexible closure 89 extends radially outward from each knotter 25 for covering the slot 73 when the knotter is in its inner (retracted) position so that the vacuum may be maintained in the respective vacuum chamber 41. The closure 89 slides in a curved recess 91 at the bottom of the chamber 41 when the knotter 25 moves out to its outer (extended) position (as shown at the left in FIG. 10 and in FIG. 11). The vacuum system of the apparatus, generally designated by 93, includes flexible vacuum lines (one of which is designated by 95 at the right in FIG. 10) connected to the respective knotters 25 for creating a vacuum in the entry hole 27 of the knotter to draw the end portions of the reaches 21, 23 of the string 17 into the knotter. An actuating mechanism for the knotter (generally designated by 97 in FIG. 11) comprises a trigger 99 which engages a set screw 101 in a ring 103 supporting the outer ends of the guide rods 75 as the knotter 25 moves outward.

One needle 31 (i.e., elongate piercing tool) is mounted in each chamber 41 of the turret 37. Each needle extends radially with respect to the turret 37 through a hole 45*b* in the inner end 45*a* of the respective chamber 41. Each needle 31 moves radially lengthwise between a retracted position wherein its notched tip 33 is positioned near the inner end 45*a* of the chamber 41 and an extended position wherein the tip extends through the hole 15 of the pledget at the front of the chamber. The needles 31 are cam-controlled so that each occupies its retracted position when traveling from zone Z1 to Z4, then moves out radially with respect to the turret 37 when traveling through a zone Z5, and then moves radially inward (i.e., retracted) when moving through zone Z6.

Each needle 31 is held by a slider 107 driven along a radially extending guide rod 109. The slider 107 has cam follower rollers 111 which engage an annular cam 113 on the stationary plate 85 for moving the needle 31 between its retracted position (shown at the right in FIG. 10) and its extended position (shown at the left in FIG. 10). The slider 107 moves the needle 31 by means of a rack and pinion mechanism indicated at 115. The cam 113 is formed so each needle 31 occupies its retracted position when travelling from zone Z1 to zone Z4, moves radially outwardly when traveling through zone Z5, then back into its retracted position when traveling through zone Z6. As the needle moves forward (radially outward) from its retracted position, it captures the knotted end of the loop in the tip 33, pulling the knotted end of the loop out of the knotter 25. The needle, with the knotted end of the loop captured by its tip 33, moves forward so it extends through the hole 15 in the pledget, thereby threading the loop through the hole. Then as the needle 31 retracts when moving through zone Z6, it releases the end portion of the loop which was captured by the tip 33, leaving the end portion behind so the string 17 encircles the pledget, extending from the back face 5 of the pledget through the hole 15 and having the aforesaid double-strand string pendant 35 extending from the hole.

When the needles 31 move radially outward from their retracted position in the initial phase of zone Z5 and progress through zone Z6 to pierce the pledget 1, the pledget is held in its holder 39 by endless belts 117 and 119. Belt 117 has an inner reach 117a engaging the upper part of the front face 3 of each pledget 1 as the holders 39 carry them through zones Z5 and Z6. Belt 119, which is below belt 117, has lugs 119a spaced at intervals on the outside thereof each having a hole therein for receiving the tip of a needle 31. The lugs 119a engage the lower part of the front faces 3 of the pledgets 1 as they move through zones Z5 and Z6.

Exiting from zone Z6, the now strung pledgets 1 pass through zone Z7 and are plucked off the turret 37 out of the holders 39 by a vacuum take-off roll 121, then passed to another vacuum take-off roll 123, and taken to a downstream conveyor 125. As each chamber 41 exits from zone Z7, ending a cycle, it enters zone Z1 and another cycle is initiated.

The vacuum system may embody various suitable means for timing application of vacuum to the chambers 41 and knotters 25. For example, conventional programmable vacuum valves may be used.

Thus, the invention involves stringing tampon pledgets 1. Each pledget 1 has a front face 3 and a back face 5 and a hole 15 extending therethrough. The series of pledget holders 39 spaced at intervals around the periphery of the turret 37 are rotated around in a circular path. A pledget 1 is placed in each holder 39 in the first zone Z1 so the front face 3 of the pledget faces outward. String S is fed to each pledget at the second zone Z2 farther along the circular path by the string feeder 55, so a length of the string 17 extends across the front face 3 of the pledget 1 with a central portion 19 on the front face and reaches 21, 23 extending out from both sides 7, 9 of the pledget. The string is cut at the third zone Z3 farther along the circular path by the string cutter 67 to provide a length of the string (e.g., a 15.5 inch length). A looping vacuum drawn through line 72 acts on the reaches 21, 23 in the fourth zone Z4 farther along the path to draw them back around the sides 7, 9 of the pledget 1 thereby forming the string into the loop L around the pledget extending back into the chamber 41. The end portions of the reaches 21, 23 in the loop L are drawn into the knotter 25 by suction induced by vacuum drawn through line 95 and are knotted together (tied together to form the knot 29) in the knotter as the pledget 1 travels through the fifth zone Z5 farther along the path. Then, in zone Z6 farther along the path, the respective needle 31 moves radially outward over the knotter 25, capturing the loop in the tip 33 of the needle and driving the loop through the hole 15 in the pledget. Finally, in the final zone Z7, the pledget with the withdrawal string is taken away from the turret 37, and the process repeats.

In view of the above, it will be seen that several objects are achieved and other advantageous results attained.

As various changes could be made in the above constructions without departing from the scope of the invention, it is intended that all matter contained in the above description and shown in the accompanying drawings shall be interpreted as illustrative and not in a limiting sense.

When introducing elements of the present invention or various embodiment(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. Apparatus for applying a withdrawal string to a tampon pledget having opposite faces, comprising:
    a string feeder for positioning a string to extend across one of the faces of the pledget, said string thereby having a generally central portion on said one face and reaches extending on both sides of the pledget,
    a pneumatic system operable on said reaches pneumatically to form the string into a loop looped around the pledget,
    a knotter for knotting together end portions of the reaches in the loop, and
    a probe movable to drive the knotted end portion of the loop through the pledget thereby bringing part of the loop including the secured-together end portions thereof to extend out from said one face of the pledget.

2. Apparatus as set forth in claim 1 operable on pledgets having a hole extending therethrough from face-to-face, said probe being movable through said hole.

3. Apparatus for applying a withdrawal string to a tampon pledget having opposite faces, said apparatus comprising:
    a pledget holder for holding a pledget with said faces generally exposed, one constituting the front face, the opposite face the back face,
    a string feeder for feeding string to the pledget, to provide a length of string extending across said front face of the pledget, and having a generally central portion on said front face and reaches extending out from both sides of the pledget,
    a cutter for cutting the string to provide said length as a withdrawal string,
    a vacuum chamber backing the holder for applying a vacuum to act on the said reaches to draw them back around the sides of the pledget thereby forming the cut-off length of string into a loop looped around the pledget,
    a knotter in back of the holder for entry therein of the end portions of the reaches in the loop and knotting them together, and a probe for driving the knotted end portion through the pledget thereby bringing part of the loop including the knotted end thereof to extend out from said front face of the pledget.

4. Apparatus as set forth in claim 3 operable on pledgets having a hole extending therethrough from face-to-face, said probe being movable through said hole.

5. Apparatus for stringing tampon pledgets having opposite faces, said apparatus comprising:

a pledget conveyor having a series of pledget holders spaced at intervals thereon, each holder being formed for holding a pledget with its said faces generally exposed, one face facing outward and constituting the front face, the other facing inward and constituting the back face, said conveyor being movable to convey said holders in an endless path, a pledget being placed in each holder at a first zone along said path, a string feeder for feeding string to each pledget at a second zone along said path, a length of the string extending across said front face of the pledget and having a generally central portion on said front face and reaches extending out from both sides of the pledget, a cutter for cutting the string at a third zone along said path to provide said length as a withdrawal string, a series of vacuum chambers carried by the conveyor backing the holders for applying a vacuum to act on said reaches in a fourth zone along said path, to draw them back around the sides of the respective pledget thereby forming the cut-off length of string into a loop looped around the pledget, a knotter in back of the holder for entry of the end portions of the reaches in the loop and knotting them together in a fifth zone, and a probe extending in said vacuum chamber movable therein in a sixth zone for driving the knotted-together end portions of the loop through the pledget in a sixth zone along said path.

6. Apparatus as set forth in claim 5 operable on pledgets having a hole extending therethrough from face-to-face, said probe capturing the knotted loop in the tip thereof and driving the knotted loop through the hole.

7. Apparatus as set forth in claim 5 wherein said pledget conveyor comprises a rotary turret which carries pledgets in the holders around in a circular path.

8. Apparatus as set forth in claim 7 wherein each knotter is movable radially with respect to the turret toward and away from a respective pledget holder and has a hole for entry of the reaches for being knotted by suction produced by drawing a vacuum.

9. Apparatus as set forth in claim 8 operable on pledgets having a hole extending therethrough from face-to-face, said probe capturing the knotted loop in the tip thereof and driving the knotted loop through the hole, said probe being movable over said knotter.

\* \* \* \* \*